United States Patent [19]

Campbell, Jr.

[11] Patent Number: 5,092,889

[45] Date of Patent: Mar. 3, 1992

[54] EXPANDABLE VERTICAL PROSTHETIC RIB

[76] Inventor: Robert M. Campbell, Jr., 415 Stone Wood, San Antonio, Tex. 78216

[21] Appl. No.: 338,227

[22] Filed: Apr. 14, 1989

[51] Int. Cl.$^5$ .............................................. A61F 2/28
[52] U.S. Cl. ..................................... 623/16; 623/17; 606/71; 606/74
[58] Field of Search ...................... 606/60, 63, 74, 69, 606/70, 71; 623/16, 17; 128/69

[56] References Cited

U.S. PATENT DOCUMENTS

| | | | |
|---|---|---|---|
| 3,426,364 | 2/1969 | Lumb | 623/17 |
| 4,085,744 | 4/1978 | Lewis et al. | 128/69 |
| 4,096,857 | 6/1978 | Cramer et al. | 606/71 X |
| 4,201,215 | 5/1980 | Crossett et al. | 24/370 X |
| 4,279,248 | 7/1981 | Gabbay | 606/71 |
| 4,327,715 | 5/1982 | Corvisier | 623/16 |
| 4,606,335 | 8/1986 | Wedeen | 606/74 X |
| 4,611,582 | 9/1986 | Duff | 128/69 |
| 4,657,550 | 4/1987 | Daher | 623/17 |
| 4,738,251 | 4/1988 | Plaza | 128/69 |
| 4,815,453 | 3/1989 | Cotrel | 128/69 |

FOREIGN PATENT DOCUMENTS

| | | | |
|---|---|---|---|
| 0322334 | 6/1989 | European Pat. Off. | 623/17 |
| 2821678 | 11/1979 | Fed. Rep. of Germany | 128/69 |
| 0156570 | 9/1982 | Fed. Rep. of Germany | 606/71 |
| 3729600 | 3/1989 | Fed. Rep. of Germany | 623/17 |
| 0286136 | 11/1970 | U.S.S.R. | 606/71 |
| 0313538 | 10/1971 | U.S.S.R. | 128/69 |
| 0602173 | 4/1978 | U.S.S.R. | 128/69 |
| 0610518 | 6/1978 | U.S.S.R. | 606/71 |
| 1517161 | 7/1978 | United Kingdom | 606/71 |

OTHER PUBLICATIONS

Singh, et al, "A New Prosthesis for Reconstruction of Congenital Flail Chest," *British Journal of Surgery*, May 1971, vol. 58, p. 366, et seq.

Cotton, et al, "Prothesis Following Excision of Chest Wall Tumors," *Journal of Thoracic Surgery*, 1955, p. 45.

Sherman, et al, "Chest Wall Stabilization Using Plat Fixation," *The Annals of Thoracic Surgery*, Oct. 1988, p. 467, et seq.

Heaney, et al, "Unusual Problems in Management of Chest Wall Defects," *Journal of Thoracic Surgery*, 1954, p. 23.

Kinsella, et al, "Two Unusual Tumors of the Sternum," *Journal of Thoracic Surgery*, 1946, p. 640.

*Primary Examiner*—David J. Isabella
*Assistant Examiner*—David H. Willse

[57] ABSTRACT

Applicant's invention includes a prosthetic rib which is adjustable in length through relatively minor surgical procedures subsequent to initial implantation along with methods for using same in the treatment of chest wall deformities and scoliosis and in immobilizing fractured ribs. The prosthesis is designed for secure attachment to existing natural ribs in a manner which minimizes constricture thereof, provides substantial torsional stability, and permits the prothesis to accommodate traumatic impact thereto while resisting fracture of the associated natural ribs.

34 Claims, 7 Drawing Sheets

CHEST DEFECT

FIG. 7b

SPECIFIC "UNDER CARRIAGE"

EXPANDABLE VERTICAL PROSTHETIC RIB

BACKGROUND OF THE INVENTION

1. Field of the Invention

Applicant's invention relates to prosthetic skeletal devices primarily for use in humans.

2. Background Information

Presently, ribs which are missing due to trauma or congenital defect may be prosthetically replaced to a limited degree. The presently available prosthesis consists of one or more steel rods attached to and spanning vertically between existing natural ribs. This creates an artificial albeit perpendicularly oriented substitute for the missing ribs and vital protection for the cardiovascular and peripheral tissues.

The presently available prosthesis has significant limitations, the most notable of which when used in children is its inability to accommodate growth. As a child grows the distance between any two natural ribs increases. To prevent substantial disfigurement, possible injury to the spinal column, and constriction of the cardiovascular system, the radical surgical procedure of implanting the presently available prosthesis must be repeated periodically to implant longer prostheses.

SUMMARY OF THE INVENTION

It is an object of the present invention to provide a novel prosthetic rib which is adjustable in length.

It is another object of the present invention to provide an novel prosthetic rib which has means for secure attachment to existing ribs yet minimizes ischemia and accommodates benign movement and reorientation of the rib.

It is another object of the present invention to provide a prosthetic rib which accommodates traumatic impact in a manner which minimizes the risk of fracture of natural ribs to which the prosthesis is attached.

It is another object of the prevent invention to provide a prosthetic rib which provides an optimal balance between effective prosthesis and safety in implantation.

It is yet another object of the present invention to provide a prosthetic rib which may be indefinitely implanted in a child notwithstanding later growth of such child.

In satisfaction of these and related objectives, Applicant's present invention provides a prosthetic rib which is adjustable in length through relatively minor surgical procedures subsequent to initial implantation. The prosthesis is designed for secure attachment to existing natural ribs in a manner which minimizes constricture thereof, provides substantial torsional stability, and permits the prosthesis to accommodate traumatic impact thereto while resisting fracture of the associated natural ribs.

BRIEF DESCRIPTION OF THE DRAWINGS

FIG. 14b is a representation of the tips of the pliers shown in FIG. 14a.

FIG. 16b is a representation of the sheet of medical elastomeric plastic material of FIG. 16a.

DETAILED DESCRIPTION OF THE PREFERRED EMBODIMENT

Figures 1, 2A:
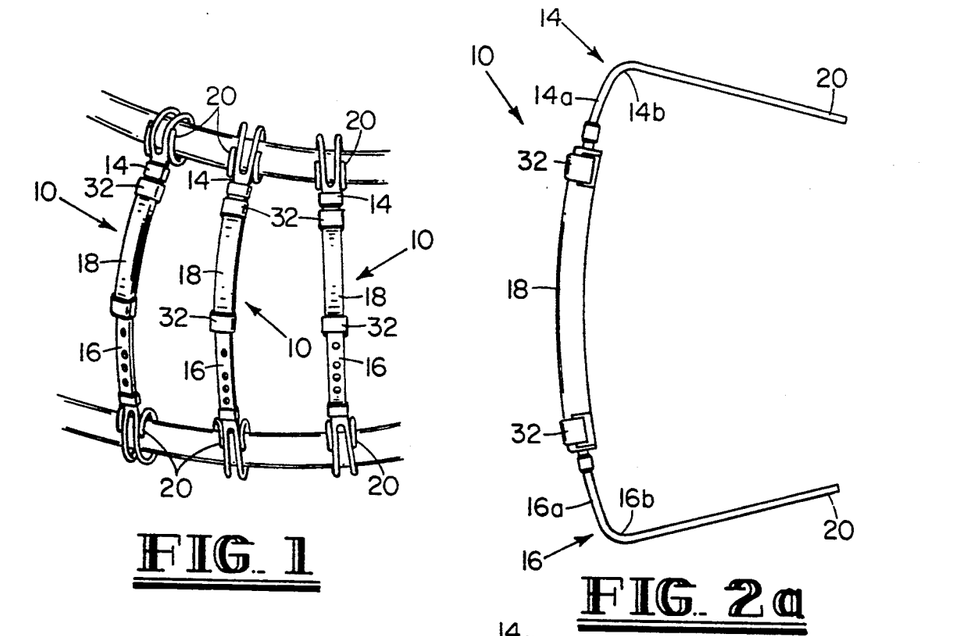
FIG. 1 is a perspective view of a number of implanted prosthetic ribs of applicant's design.
FIG. 2a is an elevational view of the prosthetic rib of Applicant's invention in a contracted configuration rib sleeve being shown as transparent.

Referring to FIG. 1, the prosthetic rib of Applicant's invention is identified generally by the reference numeral 10. As is apparent from FIG. 1, multiple prosthetic ribs 10 will typically be implanted to span between existing natural ribs 12 to compensate for an abnormal absence of intervening natural ribs.

The prosthetic rib 10 is designed to be adjusted in length subsequent to implantation. The primary purpose of the adjustability being to accommodate growth of a child in whom the prosthetic rib 10 is implanted.

Figure 2B:
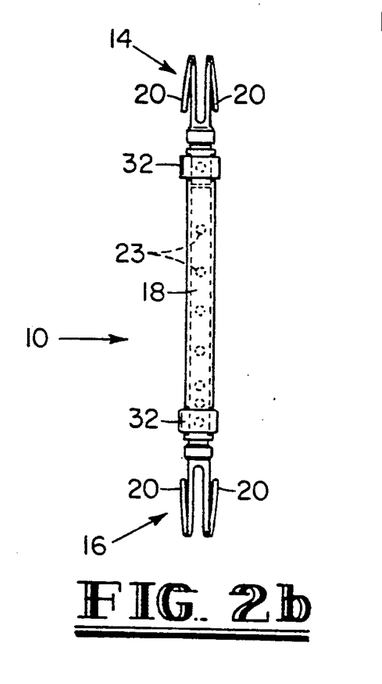
FIG. 2b is a top plan view of the prosthetic rib of Applicant's invention in a contracted configuration with the rib sleeve being shown as transparent.
Figure 2C:
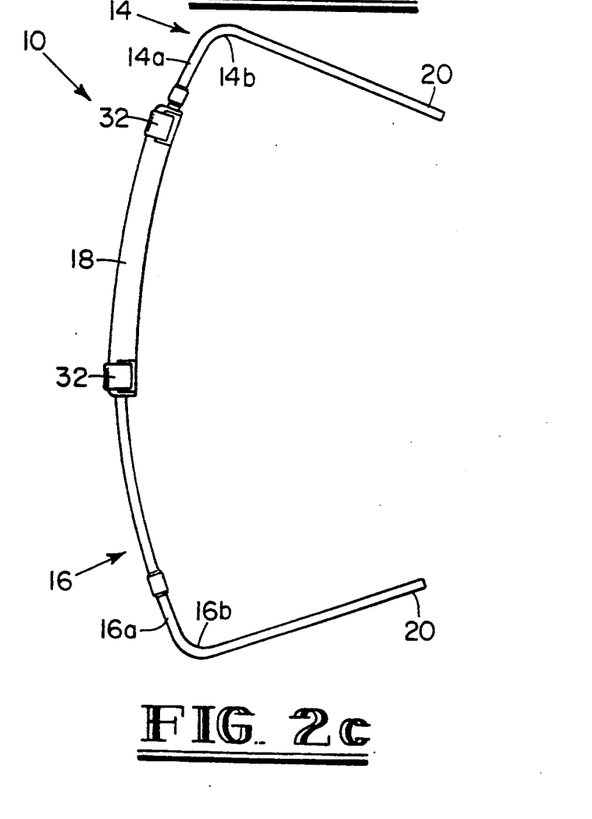
FIG. 2c is an elevational view of the prosthetic rib of Applicant's invention in an extended configuration.

Referring to FIGS. 2a, 2b, and 2c, the prosthetic rib 10 comprises three principal components: a rib sleeve carriage attachment 14, a rib shaft/rib shaft carriage attachment 16 and a rib sleeve 18. The rib shaft/rib shaft carriage attachment 16 is a single object of unitary construction, but for discussion purposes may be divided between the rib shaft 16a and the rib shaft carriage attachment 16b.

Unless otherwise specified, all components of the prosthetic rib 10, except the rib sleeve 18, which is made of Titanium Alloy 64, are manufactured of Commercially Pure (CP) Titanium. The use of titanium is dictated by the strength and flexibility requirements for the components of the prosthetic rib 10 in light of the dimensions of such components. Other materials, such as surgical grade stainless steel, may be used in constructing the prosthetic rib 10, but at the expense of the optimum balance of benefits derived from titanium.

The combined rib shaft 16a and rib sleeve 18 serve as the actual prosthesis. The robs 20 of the carriage attachments 14 and 16b serve as the attachment means for anchoring the prosthetic rib 10 to natural ribs 12 and will be discussed in detail hereinafter.

Figures 3A, 3C:
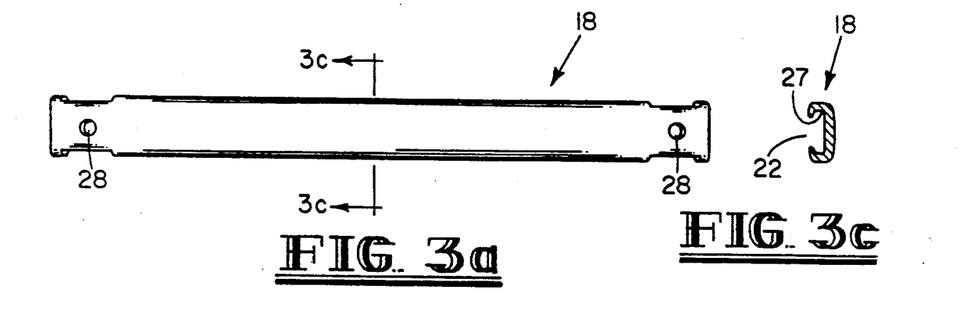
FIG. 3a is a top plan view of the rib sleeve of Applicant's invention.
FIG. 3c is a cross sectional view of the rib sleeve of Applicant's invention.
Figure 3B:
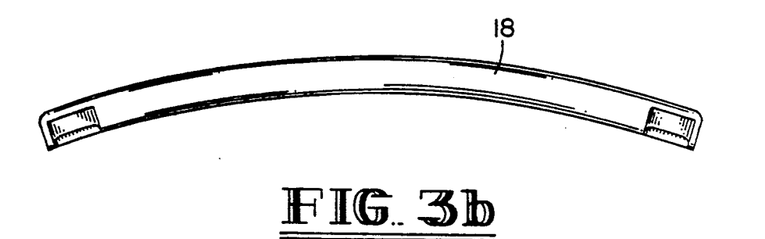
FIG. 3b is an elevational view of the rib sleeve of Applicant's invention.

Referring again to FIGS. 2a, 2b, and 2c and also to FIGS. 3a, 3b, and 3c, the rib sleeve 18 may be described as an open, semi-oval with a lengthwise oriented channel 22 interrupting the lower surface of the rib sleeve 18. The presence of the channel 22 is in response to manufacturing cost limitations. It should be understood that a suitable alternative sleeve which lacks the channel 22 entirely (not shown in the drawings) would be acceptable for the purposes stated herein, but would be available, if at all, at a considerably higher price because of difficulties in manufacturing such a sleeve.

Figure 4A:
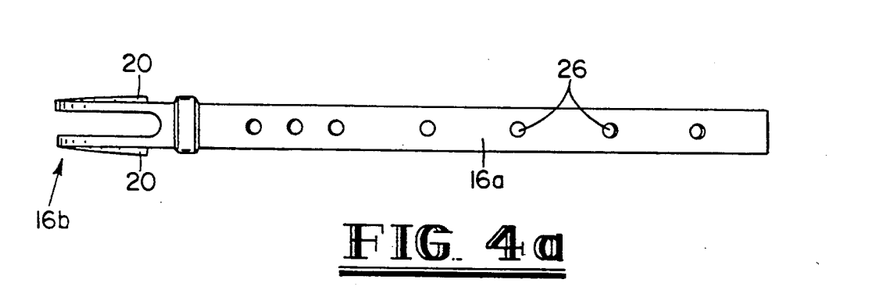
FIG. 4a is a top plan view of the rib shaft/rib shaft carriage attachment of Applicant's invention.
Figure 4B:
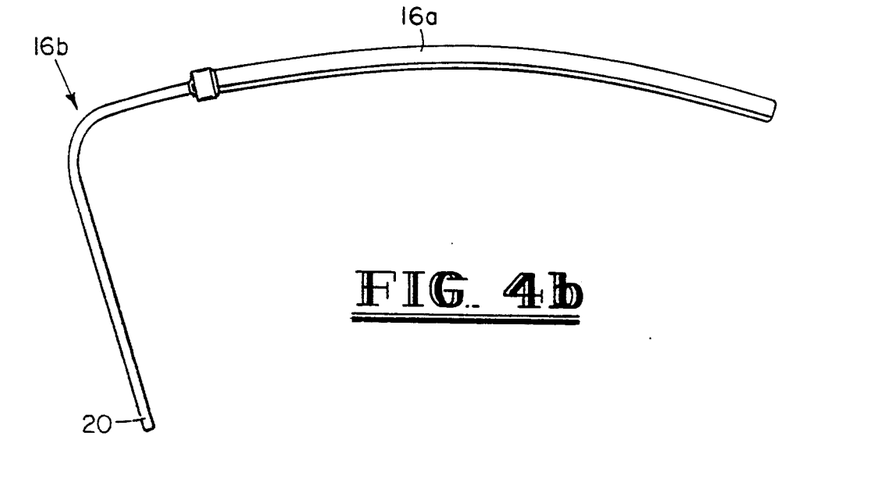
FIG. 4b is a partial elevational view of the rib shaft/rib shaft carriage attachment of Applicant's invention.
Figure 5A:
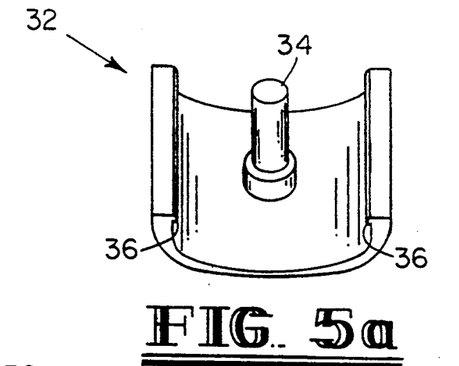
FIG. 5a is a perspective view of the inner surface of the distraction lock of Applicant's invention.
Figure 5B:
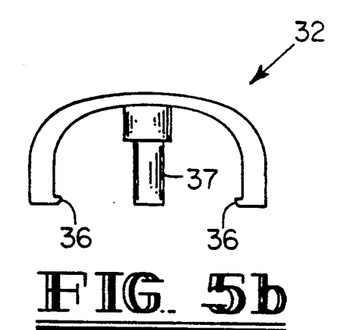
FIG. 5b is an elevational view of the inner surface of the distraction lock of Applicant's invention.
Figure 5C:
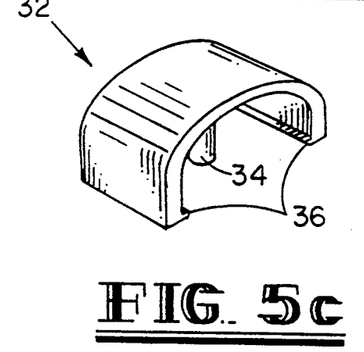
FIG. 5c is a perspective view of the outer surface of the distraction lock of Applicant's invention.
Figure 5D:
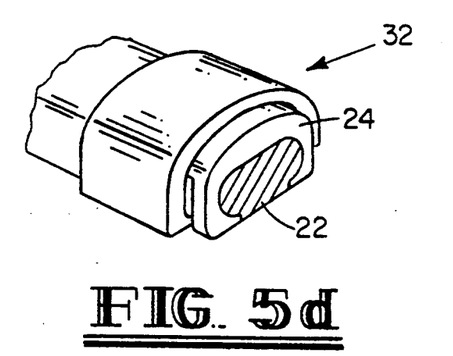
FIG. 5d is a perspective view of the distraction lock of Applicant's invention placed on a length of the rib sleeve.

Referring again to FIGS. 2a, 2b, 2c, and also to FIGS. 4a and 4b, the rib shaft 16a is of solid construction and has a lengthwise oriented ridge (not visible in the drawings). The ridge is designed to mechanically interface with the channel 22 when the rib shaft 16a is telescopically received within interior lumen 24 of the rib sleeve 18 as it is designed to do. While the presence of the channel does tend to weaken the rib sleeve 18 in resisting axial rotation relative to the rib shaft 16a, or vice versa, when a torque is applied to either, the restraining action of the ridge's interface with the channel 22 compensates completely for any such tendency. Prior to incorporating the ridge into the rib shaft 16a design, experimentation revealed a marked tendency toward such rotation particularly when the prosthetic rib 10 was extended to near its maximum extent.

The rib shaft 16a and the rib sleeve 18 are formed whereby they jointly define a single arc having a constant radius of curvature regardless of the degree the rib shaft 16a is received within the rib sleeve 18. The rib sleeve's 18 and rib shaft's 16a radius of curvature may be adjusted in the manufacturing process according to the expressed preference of the responsible surgeon, as dictated by the physiology of the intended recipient.

Referring principally to FIG. 2a, 2b, 2c, 3a, 3b, 3c, 4a and 2b, the effective length of the prosthetic rib 10 is determined by the degree to which the rib shaft 16a is telescopically received within the rib sleeve 18. To secure the relative positions of the rib shaft 16a and the rib sleeve 18 once a desired length is attained, the rib shaft 16a has a plurality of evenly spaced holes 26 passing therethrough. The rib sleeve 18 has two holes 28 spaced complementarily to the holes 26 in the rib shaft 16a. The holes 28 in the rib sleeve 18 are situated on the outer face of the rib sleeve 18. The rib sleeve carriage attachment 14 also has one hole 30 passing through its sleeve engaging projection 14a.

The holes 26, 28, and 30 are oriented whereby a linear object may concurrently extend through one of holes 26 in the rib shaft 16a and one of the two holes 28 in the rib sleeve 18 when the rib shaft 16a is telescopically received within one end of the rib sleeve 18. Likewise, a second linear object may extend through hole 30 in the rib sleeve attachment carriage 14 and through the hole 28 in the rib sleeve 18 when the sleeve projection 14a is telescopically received and properly positioned within the other end of the rib sleeve 18.

Referring principally to FIGS. 5a, 5b, 5c and 5d, once the rib shaft 16a and the rib sleeve 18 are properly, relatively positioned, they are secured using a distraction lock 32. The distraction lock 32 includes a pin 34 long enough to extend through either holes 28 and 26 or through holes 28 and 30 when in position on the assembled prosthetic rib 10, but not long enough to extend beyond the termini of the gripper flanges 36. The tip of the pin 34 as well as the termini of the gripper flanges 36 are rounded. The limit on the length of the pin 34 and the just-referenced rounding are in satisfaction of safety concerns. Sharp edges and slender protrusions are to be avoided in anticipation of the distraction lock 32 possibly becoming dislodged after implantation and have been so avoided in Applicant's preferred embodiment of the distraction lock.

The holes 26 have been spaced in 10 mm intervals in anticipation of the likely growth intervals which will indicative an adjustment of the prosthetic rib 10. Such spacing is in recognition of the fact that only slight misalignment of the spinal column can result in discomfort and possible spinal cord injury.

Referring principally to FIGS. 2a, 2b, 2c, 4a 4b, 6a and 6b, both the rib sleeve carriage attachment 14 and the rib shaft carriage attachment 16b include two rods 20 at their respective ends. The robs 20 are round in cross section. The rods 20 have a cross sectional diameter of 2 mm in the preferred embodiment.

Figure 6A:
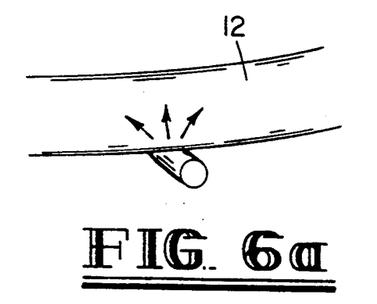
FIG. 6a is a depiction of the rounded rod of Applicant's invention as it contacts the natural rib of a recipient.
Figure 6B:
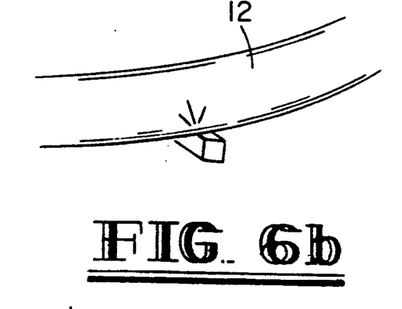
FIG. 6b is a depiction of the an angular rob, a taught against by Applicant's invention, as it would contact the natural rib of a recipient.

The rods' 20 round cross sectional shape was chosen as a means for minimizing the biological trauma to the periosteum of the ribs 12 and to the inferior surfaces of the ribs 12 where the rods 20 have their primary contact therewith (to be discussed in more detail hereinafter).

The specific 2 mm diameter of the rods 20 was chosen after numerous alternative specifications were tested. A 2 mm diameter of CP Titanium has proven to provide the optimum balance between the flexibility necessary for safe manipulation during implantation and strength necessary for post-implantation stability. No other material tested in a 2 mm rod configuration and no other dimension in CP Titanium provided the preferred characteristics for the rods 20.

The rods 20 of the preferred embodiment are 76 mm in length. This length has been shown through experimentation to provide a quite acceptable degree of surplus length to facilitate the needed manipulation during implantation both to circumvent the natural ribs 12 at the basic level, as well as to adjust the orientation and position of the loops formed from the rods 20 in determining the over-all orientation of the prosthetic rib 10 within the patient. The indicated length does not, however, introduce excessive length which would impede maneuvering during implantation and require excessive bending to avoid surrounding tissues.

Referring principally to FIGS. 1, 7a, 7b, 7c and 7d, the rods 20 are during the implantation procedure manipulated by the surgeon to circumvent the appropriate natural rib 12. The path of the rods 20 about the natural rib 12 is essentially circular when properly implanted, even though the rib would be better described as oblong. This is an important aspect of practicing Applicant's invention for several independently significant reasons. The circular circumvention permits the carriage attachments 14 and 16b to pivot relative to the natural ribs 12. This is important, in part, because the carriage attachments 14 and 16b change orientation relative to the ribs 12 to which they are attached as the length of the prosthetic rib 10 is changed subsequent to implantation.

Figure 7A:
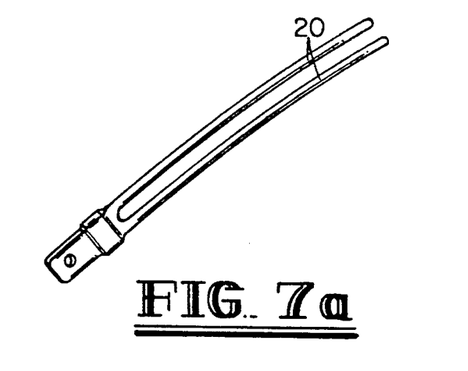
FIG. 7a is a partial perspective view of the rib sleeve carriage attachment of Applicant's invention.
Figure 7B:
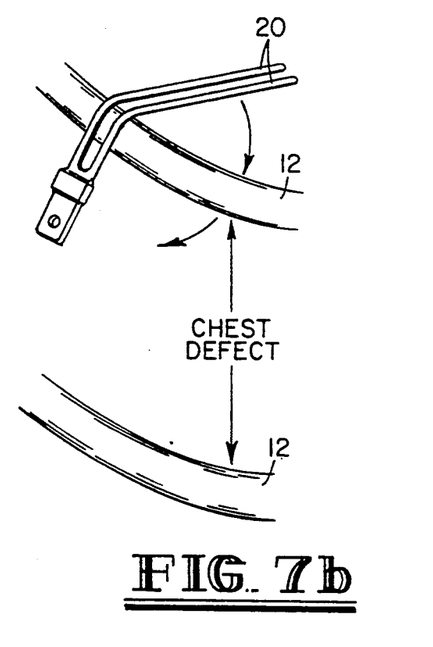
FIG. 7b is a partial perspective view of the rib sleeve carriage attachment of Applicant's invention with the rods thereof bent as for initial implantation procedures.
Figure 7C:
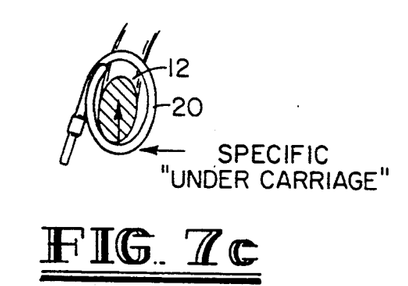
FIG. 7c is a partial perspective view of Applicant's rib sleeve carriage attachment with the rods thereof encircling a natural rib of a recipient according to the teaching of Applicant's invention.
Figures 7D, 8A:
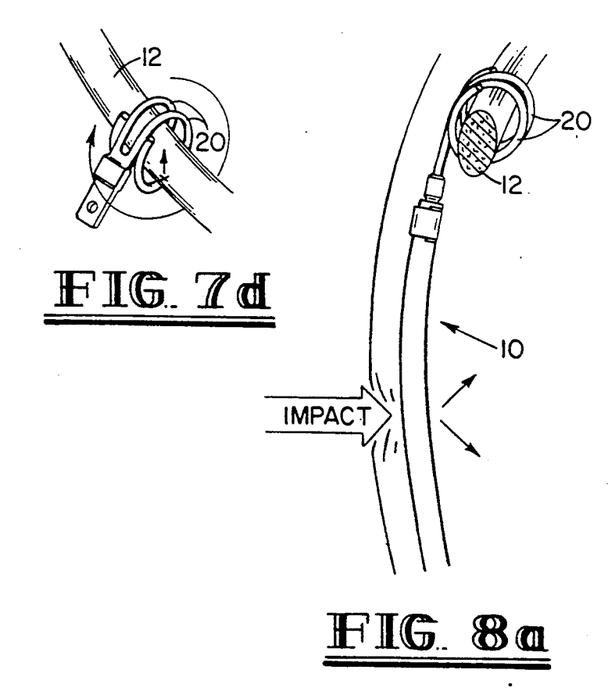
FIG. 7d is a cross sectional view of Applicant's rib sleeve carriage attachment with the rods thereof encircling a natural rib of a recipient according to the teaching of Applicant's invention.
FIGS. 8a and 8b are serial representations of the action of the Applicant's prosthetic rib in absorbing impact.
Figure 8B:
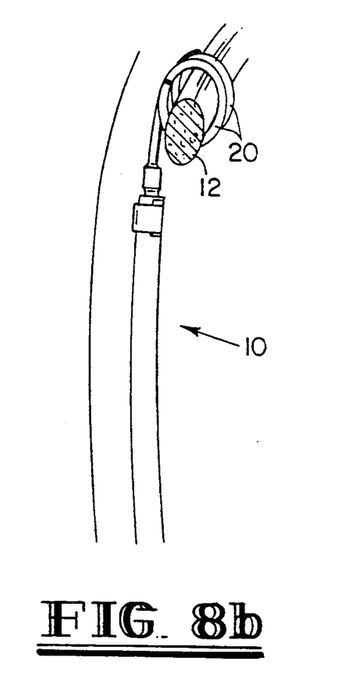

Referring principally to FIGS. 8a and 8b, the ability of the carriage attachments 14 and 16b to pivot is further important in allowing the prosthetic rib 10 to partially accommodate traumatic force which may occur in falls, etc. while not transferring the force to the natural ribs 12 in a manner which would likely fracture the natural ribs 12. If the carriage attachments 14 and 16b were rigidly attached to natural ribs 12, the carriage attachments 14 and 16b would apply a possibly damaging torque to the natural ribs 12 in response to a traumatic force to the rib shaft 16a and/or rib sleeve 18. This is substantially avoided by the circular path of circumvention suggested herein. Also, the relatively loose circumvention of the natural ribs 12 obviates the danger of rib ischemica at the site of contact between the rods 20 and the natural rib 12 surface. Still further, the gentle movement permitted by the preferred mode of attachment for the prosthetic rib 10 and brought about by normal movement of the recipient has the tendency to promote work hypertrophy thereby actually strengthening the natural rib 12.

When the prosthetic rib 10 is properly implanted and adjusted, the rods' 20 principal contact with the natural ribs 12 are to inner surface areas of the natural ribs 12 relative to the intervening chest wall defect. In this manner, the rods 20 "cradle" the natural ribs 12 at a point of minimum contact as opposed to deleteriously compressing them.

Figure 9A:
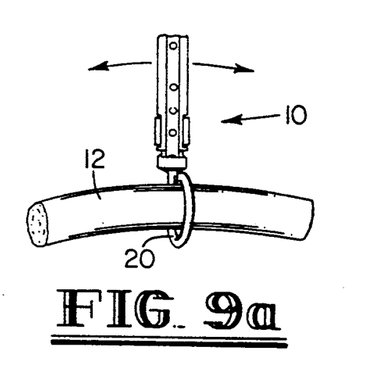
FIG. 9a is a perspective representation of a means of attachment not taught by Applicant shown to demonstrate the comparative stability of Applicant's preferred embodiment.
Figure 9B:
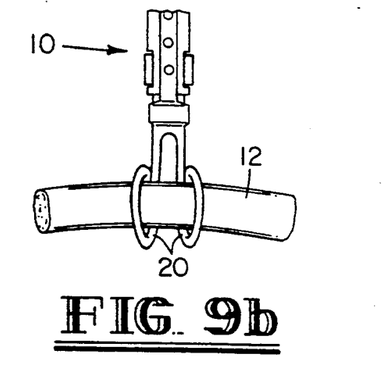
FIG. 9b is a partial perspective representation of one of Applicant's carriage attachments depicting the stability provided by the dual robs included therein.
Figure 10:
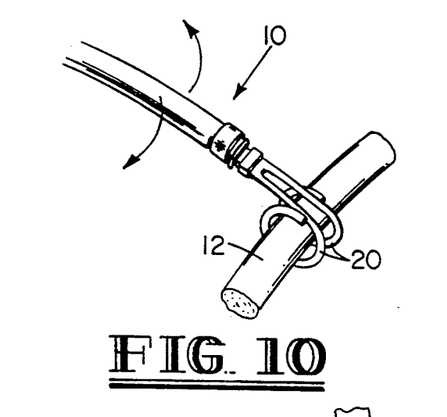
FIG. 10 is a partial perspective representation of one of Applicant's carriage attachments depicting the stability provided by the dual rods included therein.

Referring principally to FIGS. 9a, 9b and 10, the rods 20 number two for each of the carriage attachments 14 and 16b in satisfaction of some of Applicant's material objectives in designing the preferred embodiment. Most notably, dual attachment sites for the carriage attachments 14 and 16b, as opposed to a singular attachment site, provide substantial rotational stability for the prosthetic rib 20. As illustrated by FIGS. 9a and 9b, a single site of attachment will do little to stabilize the prosthetic rib 10 against even minor deflective forces while a dual attachment quite ably resists such force. Also, the cumulative mass of titanium needed for strength of the attachment to the natural ribs 12 can be divided between the two rods 20 as opposed to being embodied in a single, larger rod. Such a single rod would be too stiff to safely manipulate during implantation if it incorporated the same quantum of titanium as is divided between the two rods 20 of each carriage attachment 14 and 16b of the preferred embodiment.

It is noted that the use of three or more rods 20 is not recommended because of the associated consumption of surface space on the natural ribs 12 and the minimal additional stability which would be achieved. Because of a plurality of prosthetic ribs 10 will be required in most situations requiring any use of the prosthetic rib 10, conservation of natural 12 rib surface space is desired.

Figure 11A:
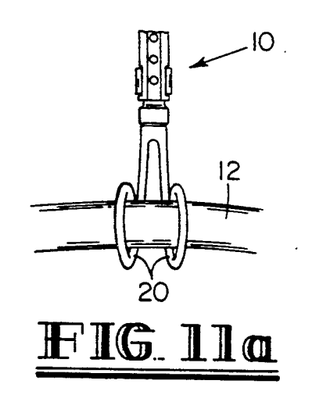
FIGS. 11a and 11b are elevational representations of one of Applicant's carriage attachments with the rods thereof affixed to the natural rib whereby the prosthetic rib projects perpendicularly from the rib surface.
Figure 11B:
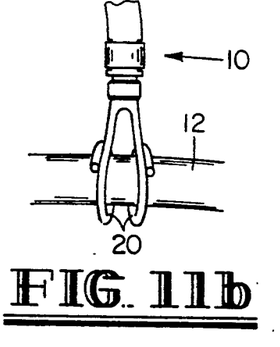
Figure 11C:
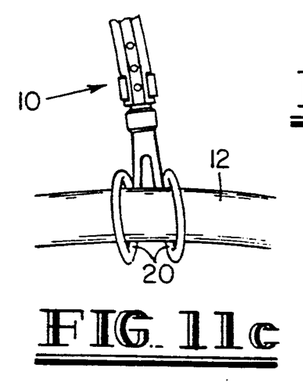
FIGS. 11c and 11d are elevational representations of one of Applicant's carriage attachments with the rods thereof affixed to the natural rib whereby the prosthetic rib projects obliquely from the rib surface.
Figure 11D:
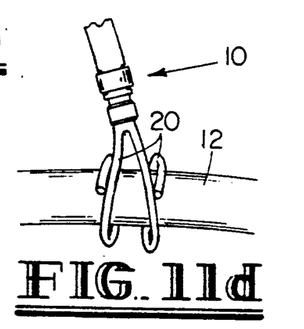
Figure 12:
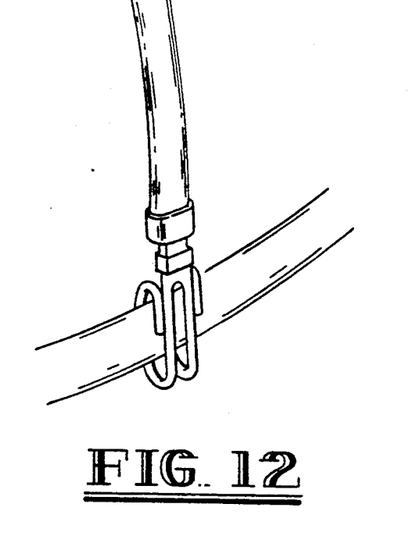
FIG. 12 is a representation of one of Applicant's carriage attachments with the rods thereof affixed to the natural rib is aligned with the vertical axis of the recipient's body notwithstanding the transverse projection of the natural rib.

Referring principally to FIGS. 11a, 11b, 11c, 11d, and 12, a perhaps less apparent benefit of dual rods 20 with a certain degree of surplus length lies in the flexibility provided to the surgeon ni orienting the prosthetic rib 10 relative to the natural ribs 12 to which the prosthetic rib 10 is attached. As shown in FIG. 12, the portions of the ribs 12 to which a prosthetic rib 10 is attached are seldom precisely perpendicular to the desired lengthwise orientation of the prosthetic rib 10. By looping the rods 20 at different positions along their length, the over-all prosthetic rib 10 can be oriented in any desired manner. Particularly where the variance from a perpendicular orientation is notably pronounced, the duel rods 20 cooperate to minimize the chance of slippage along the natural rib 12.

Referring principally to FIGS. 11c and 11d, the surgeon may not want the prosthetic rib 10 to be oriented with the convexity of the rib shaft 16a and the rib sleeve 18 extending "radially" from the patient. The dual rods 20 permit appropriate three dimensional alignment of the prosthetic rib 10 without sacrificing stability of its attachment to the natural ribs 12. The loops formed from the rods 20 may be situated in an eccentric relationship whereby the respective carriage attachment 14 or 16b is directed obliquely relative to the path of the natural rib 12.

Figure 13:
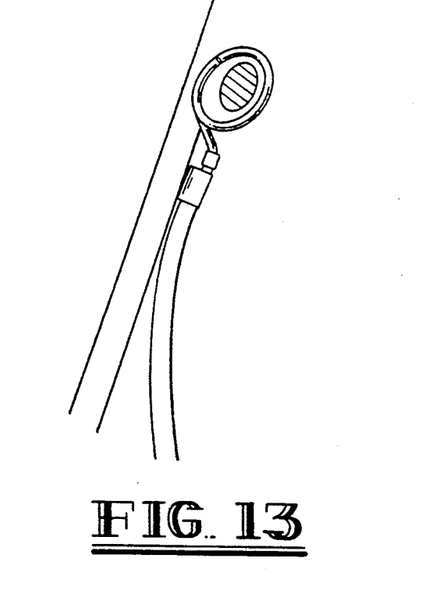
FIG. 13 is a representation of the manipulation of the rods of Applicant's carriage attachments which permits inward adjustment of the over-all prosthetic rib.

Referring principally to FIG. 13, there are occasions when anantomical considerations require that the maximum radial extension of the prosthetic rib 10 be reduced and that the respective origination and termination of the combined rib shaft 16a and rib sleeve 18 are accordingly adjusted medially relative to the outermost surfaces of the relevant natural ribs 12. The above-referenced surplus length of the rods 20 is further instrumental in permitting any such necessary adjustment as can be seen from the drawing.

The surgical procedure involved in implantation of the prosthetic rib is outlined as follows:

The patient is placed in a lateral decubitus position. The arm on the side of the procedure is free draped to allow for positioning during surgery. A longitudinal, curvi-linear incision is then made over the area of the chest wall defect and carried down to the level of the defect. The skin flaps are then developed proximal and distal and are retracted. The natural, vestigial ribs that are present proximal and distal to the chest wall defect are isolated. The prosthesis site is first selected posteriorly. The fully assembled prosthetic rib is then vertically positioned in the most posterior position of the chest wall defect, and the two rods extending from each carriage attachment are placed overlying the natural ribs and the sites are marked with a cutting cautery. The prosthetic rib is then removed and a clamp is used to pierce the intercostal muscle overlying the natural rib at each site with the lung safely held away from the camp. Thus, two holes are placed over the superior surface of the natural rib where the prosthetic rib will be placed. A similar procedure is repeated at the area immediately inferior to the natural, vestigial rib at inferior limit of the chest wall defect.

The prosthetic rib is replaced over the chest wall defect and the two rods of each carriage attachment are bent toward the chest wall cavity at a near right angle to the length of the assembled rib shaft and rib sleeve. The rods of the rib shaft carriage attachment are inserted partway through the incisions over the superior surface of the superior natural rib. The rods of the rib sleeve carriage attachment are inserted partway through the incisions under the inferior surface of the inferior natural rib.

Next, the lung is again retracted, the rib sleeve is disengaged from the rib shaft and from the rib sleeve carriage attachment so that both carriage attachments can be rotated so that the respective rods inside the chest cavity are brought out toward the surgeon for visualization in the chest wall defect. The rib shaft carriage attachments are sequentially held in place as the surgeon, using pliers or a suitable substitute, manipulates the rods to circumvent the natural ribs in a circular, minimally pitched spiral configuration with the most distal portion of each rod coming to closely juxtapose its proximal origin exterior to the chest cavity (See FIG. 15b). The only interthoracic portions of the carriage attachments are the curved, smooth surfaces of the rods.

Once the rods are configured about the natural ribs, the rib sleeve is re-engaged with the rib shaft and the engaging projection of the rib sleeve carriage attachment to allow final positioning of the prosthetic rib assembly. The radius and length of the rods are adjusted to provide final position of the actual over all prosthetic rib assembly. By appropriately bending and orienting the rods over-all position of the prosthetic rib assembly may be brought further into the chest wall defect to allow for clearance of neurovascular bundles of the arm. Also the loops formed of the rods can be adjusted to lie eccentrically to orient the rib shaft and rib sleeve in an anterior lateral or posterior lateral position.

Once final positioning of the first prosthetic rib assembly is attained, a suitable plurality of prosthetic ribs are implanted as just described in an anterior progression until the chest wall defect is adequately overlain.

Figure 15A:
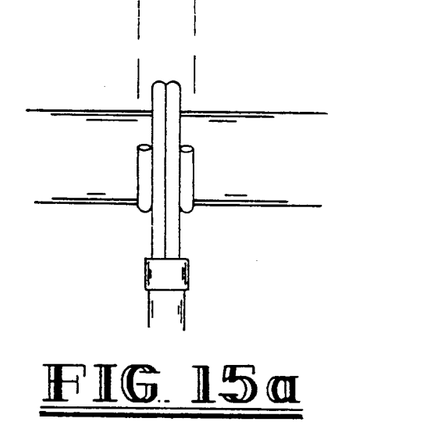
FIG. 15a is a representation of rods improperly spaced on a recipient natural rib.
Figure 15B:
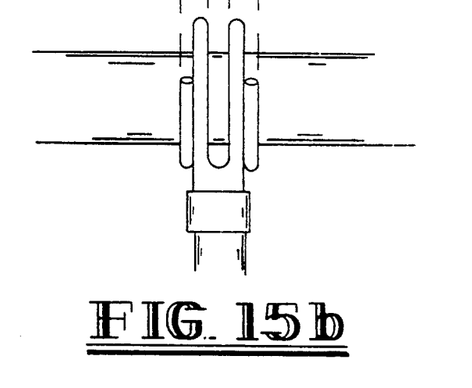
FIG. 15b is a representation of rods properly spaced on a recipient natural rib.

In the implantation procedure, care is taken that the two rods of each carriage attachment are separated by an adequate distance to allow for blood supply of the natural rib between them (See FIGS. 15a and 15b). Once the desired number of prosthetic ribs are satisfactorily in position, distraction locks installed as previously described herein.

Figure 16A:
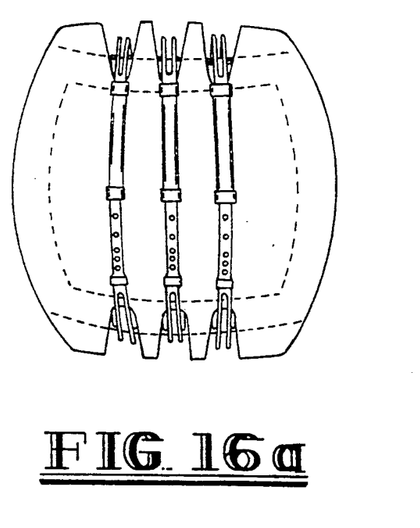
FIG. 16a is a representation of an implanted sheet of medical elastomeric plastic material underlying Applicant's prosthetic ribs.
Figure 16B:
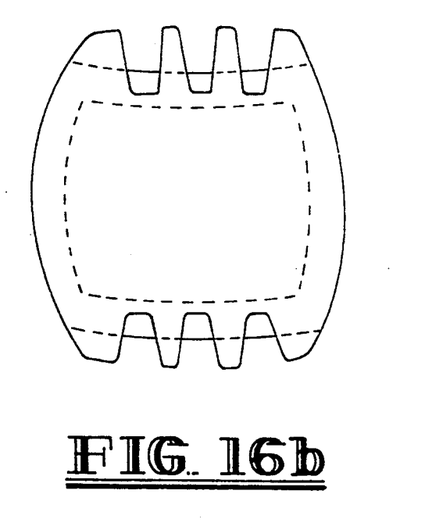

Referring to FIGS. 16a and 16b, a dacron, reinforced, Silastic sheet of at least 0.030 inch thickness is next measured to cover the chest wall defect and overlap it to a distance of approximately 2 centimeters in all dimensions. Slots are cut in the material where the carriages are piercing the chest wall and the center portion and the narrow strip of material should be threaded between the carriage shafts for each prosthesis. The silastic sheet is then placed underneath the prosthetic and provides an interface between the lung surface and the metal of the prosthesis. The periphery of the silastic sheet is sutured in each corner and, utilizing a zero proline suture, the plastic sheet is attached at two inch intervals along each prosthetic rib to tether it up to the external chest wall formed by the prosthetic ribs. Chest tubes are then inserted inside the thoracic cavity to fully expand the lugs and then the skin surface is closed in the usual surgical manner.

Figure 14A:
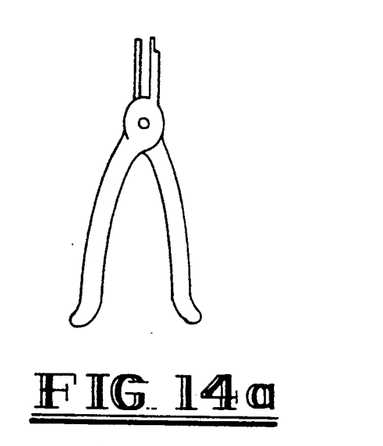
FIG. 14a is a representation of the pliers used to adjust the length of an implanted prosthetic rib.
Figure 14B:
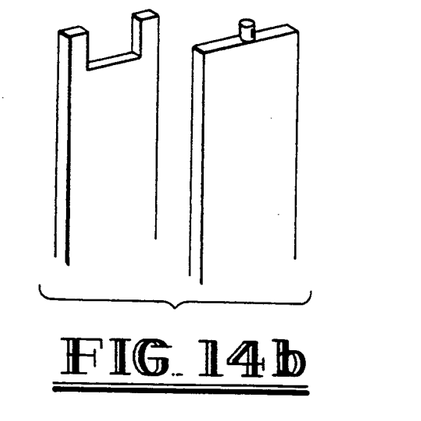
Figure 14C:
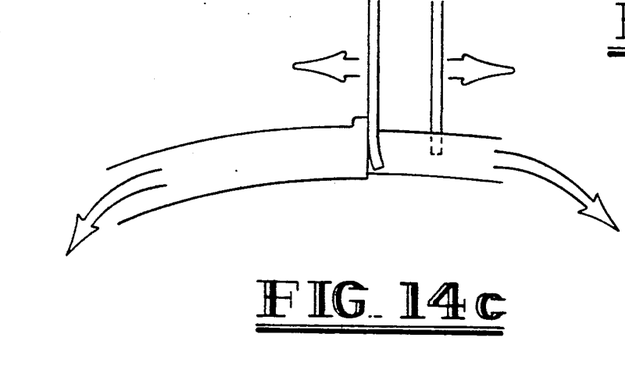
FIG. 14c is a representation of the pliers of FIG. 14a is position to adjust the rib shaft relative to the rib sleeve.

The surgical procedure involved in adjusting the length of the previously implanted prosthetic rib is outlined as follows:

The patient under general anaesthetic has an incision made in the scar from the original implantation. Once this is done the skin flap is minimally dissected down toward the distraction locks securing the rib shaft relative to the rib sleeve. Once distraction locks are located, they are removed from each of the prosthetic ribs except the central most one. Next, distraction pliers (shown in FIGS. 14a, 14b, and 14c) are engaged with the central most prosthetic rib and the last distraction lock is removed. The distraction pliers are used to lengthen the central most prosthetic rib to the desired extent to expand the affected chest cavity to the length of the normal chest cavity. Once this adjustment is performed, distraction locks are placed on all prosthetic ribs to secure their adjusted lengths and states. The silastic sheet's edges are drawn further to the edges of the actual borders of the chest wall defect and the proline suture which is tethering the silastic sheet to the undersurface of the ribs slides on top of the body of the prosthetic ribs. Once this is accomplished, a radiograph checks their final position and the skin gets closed in the usual fashion. No chest tubes are needed.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:
1. A prosthetic rib comprising:
an elongate shaft member configured to be expandable and retractable in length and having locking means operably associated therewith for reversibly locking said shaft member to one of a plurality of substantially fixed lengths which are selectible both before and after implantation of said prosthetic rib;
stabilizing means for securing said prosthetic rib to distinct, spatially separated skeletal components of a recipient of said prosthetic rib, said stabilizing means for attachment to said skeletal components in a manner for alternatively effecting compressive and distractive forces on said skeletal components for maintaining a substantially fixed relative spacing between said skeletal components substantially as determined by said length of said shaft member.

2. The invention of claim 1 wherein said stabilizing means comprises a plurality of rods, at least one said rod being affixed at respective outer ends of said first and second prosthetic rib members, said rods being of a malleable material and of a length whereby said rods may be manipulated to encircle a natural rib of said recipient and thereby secure said prosthetic rib within said recipient.

3. The invention of claim 1 wherein said stabilizing means comprises first and second pairs of rods being respectively affixed to outer ends of said first and second prosthetic rib members, each of said rods being made of a sufficiently malleable material and being of a sufficient length, when measured parallel with the length of said first and second prosthetic rib members, whereby said rods may be manipulated to encircle a natural rib of said recipient and thereby secure said prosthetic rib within said recipient.

4. A prosthetic rib comprising:
a prosthetic rib shaft having a lateral prosthetic rib shaft end and a medial prosthetic rib shaft end;
a prosthetic rib sleeve, said prosthetic rib sleeve having a lateral prosthetic rib sleeve end, a medial prosthetic rib sleeve end, and a channel opening at said medial prosthetic rib sleeve end for telescopically receiving said rib shaft at its said medial prosthetic rib shaft end;
prosthetic rib shaft stabilizing means affixed to said lateral prosthetic rib shaft end and oriented for securing said prosthetic rib shaft to a first rib of a recipient of said prosthetic rib in an orientation substantially perpendicular to the length of said first rib by loosely encircling said first rib;
prosthetic rib sleeve stabilizing means affixed to said lateral prosthetic rib sleeve end and oriented for securing said prosthetic rib sleeve to a second rib of a recipient of said prosthetic rib in an orientation substantially perpendicular to the length of said second rib by loosely encircling said second rib;
said prosthetic rib shaft stabilizing means and said prosthetic rib sleeve stabilizing means for securing said prosthetic rib without effecting a constrictive force on either said first rib or said second rib.

5. The invention of claim 4 wherein said prosthetic rib shaft stabilizing means comprise a plurality of rods attached to and extending outwardly from said lateral prosthetic rib shaft end parallel with said prosthetic rib shaft's length, said rods being made of a sufficiently malleable material and being of sufficient length, when measured parallel with said length of said prosthetic rib shaft, whereby said rods may be manipulated to encircle a natural rib of said recipient and thereby secure said prosthetic rib shaft within said recipient.

6. The invention of claim 4 wherein said prosthetic rib sleeve stabilizing means comprise a plurality of rods attached to and extending outwardly from said lateral prosthetic rib sleeve end parallel with said prosthetic rib sleeve's length, said rods being made of a sufficiently malleable material and being of sufficient length, when measured parallel with said length of said prosthetic rib sleeve, whereby said rods may be manipulated to encircle a natural rib of said recipient and thereby secure said prosthetic rib sleeve within said recipient.

7. The invention of claim 4 wherein said prosthetic rib shaft stabilizing means and said prosthetic rib sleeve stabilizing means each comprise a plurality of rods respectively attached to and extending outwardly from said lateral prosthetic rib shaft end and said lateral prosthetic rib sleeve end parallel with said prosthetic rib shaft's and sleeve's length, said rods being made of a sufficiently malleable material and being of sufficient length, when measured parallel with said lengths of said prosthetic rib shaft and sleeve, whereby each of said rods may be manipulated to circumvent a natural rib of said recipient and thereby secure said prosthetic rib within said recipient.

8. The invention of claim 5 wherein there are two of said rods affixed to said lateral prosthetic rib shaft end.

9. The invention of claim 6 wherein there are two of said rods affixed to said lateral prosthetic rib sleeve end.

10. The invention of claim 7 wherein there are two of said rods affixed to said lateral prosthetic rib shaft end and said lateral prosthetic rib sleeve end.

11. The invention of claim 7 wherein all surfaces of said rods in cross-section are of a curved configuration.

12. The invention of claim 10 wherein all surfaces of said rods in cross-section are of a curved configuration.

13. A prosthetic rib comprising:
a prosthetic rib shaft having a lateral prosthetic rib shaft end and a medial prosthetic rib shaft end;
a prosthetic rib sleeve, said prosthetic rib sleeve having a lateral prosthetic rib sleeve end, a medial prosthetic rib sleeve end, and channel opening at said medial prosthetic rib sleeve end for telescopically receiving said rib shaft at its said medial prosthetic rib shaft end;
a first pair of rods extending from said lateral prosthetic rib shaft end;
a second pair of rods extending from said lateral prosthetic rib sleeve end;
said prosthetic rib shaft and said prosthetic rib sleeve having a similar concavity along their respective lengths whereby said prosthetic rib shaft and said prosthetic rib sleeve jointly define an arc of a substantially constant radius of curvature regardless of the degree to which said prosthetic rib shaft is received within said channel of said prosthetic rib sleeve.

14. The invention of claim 13 wherein said rods are made from titanium, are substantially circular in cross section and have a diameter of approximate 2 mm.

15. The invention of claim 13 wherein said prosthetic rib shaft and said prosthetic rib sleeve each have a plurality of complementarily spaced holes passing fully therethrough perpendicular to their respective lengths, said holes for receiving locking means therethrough for securing said prosthetic rib shaft and said prosthetic rib sleeve in a fixed relative position.

16. The invention of claim 15 wherein said locking means are of the nature of a snap-on lock comprising a pin member for extending through said holes and first and second gripper flanges on either side of said pin, said gripper flanges being shaped whereby said interior space defined by said gripper flanges may snugly receive a length of the outer surface of said prosthetic rib sleeve when forced onto said length of outer surface against a slight resilient force applied by said gripper flanges, said pin being situated whereby said pin extends through said holes in said prosthetic rib sleeve and said prosthetic rib shaft when said lock is positioned on said length of the outer surface of said prosthetic rib sleeve, said resilient force maintaining said lock in place on said length of the outer surface of said prosthetic rib sleeve unless forcibly removed therefrom.

17. A prosthetic rib comprising:
a prosthetic rib shaft having a lateral prosthetic rib shaft end and a medial prosthetic rib shaft end;
a prosthetic rib sleeve, said prosthetic rib sleeve having a lateral prosthetic rib sleeve end, a medial prosthetic rib sleeve end, and a channel opening at said medial prosthetic rib sleeve end for telescopically receiving said rib shaft at its said medial prosthetic rib shaft end;
a first pair of rods extending from said lateral prosthetic rib shaft end, said rods being made from titanium, having a substantially circular cross sectional shape, and having a diameter of approximately 2 mm;
a second pair of rods extending from said lateral prosthetic rib sleeve end, said rods being made from titanium, having a substantially circular cross sectional shape, and having a diameter of approximately 2 mm;
said prosthetic rib shaft and said prosthetic rib sleeve having a similar concavity along their respective lengths whereby said prosthetic rib shaft and said prosthetic rib sleeve jointly define an arc of a substantially constant radius of curvature regardless of the degree to which said prosthetic rib shaft is received within said channel of said prosthetic rib sleeve;
said prosthetic rib shaft and said first pair of rods being of unitary construction and forming a first single piece of titanium and said prosthetic rib sleeve and said second pair of rods being of unitary construction and forming a second single piece of titanium;
said prosthetic rib shaft and said prosthetic rib sleeve each having a plurality of complementarily spaced holes passing fully therethrough perpendicular to their respective lengths, said holes for receiving locking means therethrough for securing said prosthetic rib shaft and said prosthetic rib sleeve in a plurality of fixed relative positions.

18. The invention of claim 17 wherein said locking means are of the nature of a snap-on lock comprising a pin member for extending through said holes and first and second gripper flanges on either side of said pin, said gripper flanges being shaped whereby interior space defined by said gripper flanges may snugly receive a length of the outer surface of said prosthetic rib sleeve when forced onto said length of outer surface against a resilient force applied by said gripper flanges said pin being situated whereby said pin extends through one said hole in said prosthetic rib sleeve and one said hole in said prosthetic rib shaft when said lock is positioned on said length of said outer surface of said prosthetic rib sleeve, said resilient force maintaining said lock in place on said length of the outer surface of said prosthetic rib sleeve unless forcibly removed therefrom.

19. A prosthetic rib comprising:
a prosthetic rib shaft having a lateral prosthetic rib shaft end and a medial prosthetic rib shaft end, prosthetic rib shaft stabilizing means being formed at said lateral prosthetic rib shaft end for securing said prosthetic rib shaft to a skeletal component of a recipient of said prosthetic rib;
a prosthetic rib sleeve, said prosthetic rib sleeve having a lateral prosthetic rib sleeve end, a medial prosthetic rib sleeve end, and a channel passing continuously through said prosthetic rib sleeve and opening at both said rib sleeve ends, said channel having dimensions whereby said medial end of said prosthetic rib shaft may be telescopically received therein;
prosthetic rib sleeve stabilizing means for securing said prosthetic rib sleeve to a skeletal component of a recipient of said prosthetic rib, said prosthetic rib sleeve stabilizing means having a sleeve stabilizing means projection with dimensions whereby said projection sleeve stabilizing means projection may be telescopically received within said channel at said lateral prosthetic rib sleeve end.

20. The invention of claim 19 wherein said prosthetic rib shaft stabilizing means comprise a plurality of rods extending from said lateral prosthetic rib shaft end, said rods being made of a sufficiently malleable material and being of sufficient length whereby said rods may be manipulated to encircle a natural rib of said recipient and thereby secure said prosthetic rib shaft within said recipient.

21. The invention of claim 20 wherein said prosthetic rib sleeve stabilizing means comprise a plurality of rods attached to and extending outwardly from said lateral prosthetic rib sleeve, said rods being made of a sufficiently malleable material and being of sufficient length whereby said rods may be manipulated to encircle a natural rib of said recipient and thereby secure said prosthetic rib sleeve within said recipient.

22. The invention of claim 21 wherein said rods comprised within said prosthetic rib sleeve stabilizing means are limited in number to two and said rods comprised within said prosthetic rib shaft stabilizing means are limited in number to two.

23. The invention of claim 21 wherein said prosthetic rib sleeve has a plurality of sleeve locking holes spaced along the length of said sleeve, said prosthetic rib shaft having a shaft locking hole passing at least partially therethrough near said medial prosthetic rib shaft end and oriented whereby a first linear pin member may pass simultaneously through one of said sleeve locking holes and into said shaft locking hole, said sleeve stabilizing means projection having a projection locking hole passing at least partially therethrough and positioned whereby a second linear pin member may pass simultaneously through a second one of said sleeve locking holes and into said projection locking hole.

24. The invention of claim 21 wherein said prosthetic rib sleeve has first and second sleeve locking holes, said first sleeve locking hole being situated near said medial prosthetic rib sleeve end and said second sleeve locking hole being situated near said lateral prosthetic rib sleeve end, said prosthetic rib shaft having a plurality of shaft locking holes spaced along the length of said shaft, passing at least partially therethrough and oriented whereby a first linear pin member may pass simultaneously through said first sleeve locking hole and into one of said shaft locking holes, said prosthetic rib sleeve stabilizing means projection having a projection locking hole passing at least partially therethrough and oriented whereby a second linear pin member may pass simultaneously through said second sleeve locking hole and into said projection locking hole.

25. The invention of claim 24 further comprising a resilient snap-on lock member comprising a pin member for extending through a first one of said shaft locking holes and said first sleeve locking hole or through said projection locking hole and said second sleeve locking hole, said lock further comprising first and second gripper flanges on either side of said pin, said gripper flanges being shaped whereby interior spaced defined by said gripper flanges may snugly receive a length of said prosthetic rib sleeve when forced thereon against a slight resilient force applied by said gripper flanges, said pin being situated whereby said pin extends through said first one of said shaft locking holes and said first sleeve locking hole or through said projection locking hole and said second sleeve locking hole when said lock is positioned on said length of said prosthetic rib sleeve, said resilient force maintaining said lock in place on said length of said prosthetic rib sleeve unless forcibly removed therefrom.

26. The invention of claim 23 further comprising a resilient snap-on lock member comprising a pin member for extending through said shaft locking hole and a first of said sleeve locking holes or through said projection locking hole and a second of said sleeve locking holes, said lock further comprising first and second gripper flanges on either side of said pin, said gripper flanges being shaped whereby interior space defined by said gripper flanges may snugly receive a length of said prosthetic rib sleeve when forced thereon against a slight resilient force applied by said gripper flanges, said pin being situated whereby said pin may extend through said shaft locking hole and a first of said sleeve locking holes or through said projection locking hole and a second of said sleeve locking holes when said lock is positioned on said length of said prosthetic rib sleeve, said resilient force maintaining said lock in place on said length of said prosthetic rib sleeve unless forcibly removed therefrom.

27. A method of prosthetically replacing natural human ribs comprising the steps of surgically accessing existing natural ribs of a recipient and attaching a prosthetic rib to said natural ribs, said prosthetic rib comprising:
   a prosthetic rib shaft having a lateral prosthetic rib shaft end and a medial prosthetic rib shaft end, prosthetic rib shaft stabilizing means being formed at said lateral prosthetic rib shaft end for securing said prosthetic rib shaft to a skeletal component of a recipient of said prosthetic rib;
   a prosthetic rib sleeve, said prosthetic rib sleeve having a lateral prosthetic rib sleeve end, a medial prosthetic rib sleeve end, and a channel passing continuously through said prosthetic rib sleeve and opening at both said rib sleeve ends, said channel having dimensions whereby said medial end of said prosthetic rib shaft may be telescopically received therein;
   prosthetic rib sleeve stabilizing means for securing said prosthetic rib sleeve to a skeletal component of a recipient of said prosthetic rib, said prosthetic rib sleeve stabilizing means having a sleeve stabilizing means projection with dimensions whereby said projection sleeve stabilizing means may be telescopically received within said channel at said lateral prosthetic rib sleeve end.

28. The method of claim 27 wherein said prosthetic rib shaft stabilizing means comprise a plurality of rods extending from said lateral prosthetic rib shaft end, said rods being made of a sufficiently malleable material and being of sufficient length whereby said rods may be manipulated to encircle a natural rib of said recipient and thereby secure said prosthetic rib shaft within said recipient.

29. The method of claim 28 wherein said prosthetic rib sleeve stabilizing means comprise a plurality of rods attached to and extending outwardly from said lateral prosthetic rib sleeve, said rods being made of a sufficiently malleable material and being of sufficient length whereby said rods may be manipulated to encircle a natural rib of said recipient and thereby secure said prosthetic rib sleeve within said recipient.

30. The method of claim 29 wherein said rods comprised within said prosthetic rib sleeve stabilizing means are limited in number to two and said rods comprised within said prosthetic rib shaft stabilizing means are limited in number to two.

31. The method of claim 29 wherein said prosthetic rib sleeve has first and second sleeve locking holes, said first sleeve locking hole being situated near said medial prosthetic rib sleeve end and said second sleeve locking hole being situated near said lateral prosthetic rib sleeve end, said prosthetic rib shaft having a plurality of shaft locking holes spaced along the length of said shaft, passing at least partially therethrough and oriented whereby a first linear pin member may pass simultaneously through said first sleeve locking hole and into one of said shaft locking holes, said prosthetic rib sleeve stabilizing means projection having a projection locking hole passing at least partially therethrough and oriented whereby a second linear pin member may pass simultaneously through said second sleeve locking hole and into said projection locking hole.

32. The method of claim 31 wherein said prosthetic rib further comprises a resilient snap-on lock member comprising a pin member for extending through a first one of said shaft locking holes and said first sleeve locking hole or through said projection locking hole and said second sleeve locking hole, said lock further comprising first and second gripper flanges on either side of said pin, said gripper flanges being shaped whereby interior space defined by said gripper flanges may snugly receive a length of said prosthetic rib sleeve when forced thereon against a slight resilient force applied by said gripper flanges, said pin being situated whereby said pin extends through said first one of said shaft locking holes and said first sleeve locking hole or through said projection locking hole and said second sleeve locking hole when said lock is positioned on said length of said prosthetic rib sleeve, said resilient force maintaining said lock in place on said length of said prosthetic rib sleeve unless forcibly removed therefrom.

33. A prosthetic apparatus comprising:
   a shaft member comprising first and second rib members movable with respect to each other whereby said shaft member is adjustable in length;
   stabilizing means for respectively securing said first and second rib members to first and second distinct, spatially separated skeletal components of a recipient of said prosthetic device, said stabilizing means comprising a plurality of rods, at least one said rod being affixed at respective outer ends of said first and second rib members, said rods being of a malleable material and of a length whereby said rods may be manipulated to encircle a natural rib of said recipient and thereby secure said prosthetic device within said recipient; and locking means operably associated with said first and second rib members for reversibly locking said shaft member to one of a plurality of substantially fixed lengths which are selectible both before and after implantation of said prosthetic rib.

34. A method for providing prosthesis in substitution for missing or damaged natural human ribs comprising the steps of surgically accessing healthy, undamaged existing natural ribs anterior and posterior to said missing or damaged ribs of a recipient and respectively, loosely attaching first and second ends of a prostatic rib to said natural ribs which are anterior and posterior to said missing or damaged ribs, said prosthetic rib comprising:

a shaft member comprising a plurality of members movably attached to each other in a manner whereby said shaft member is adjustable in length, said shaft member comprising first and second rib members, a portion of said first prosthetic rib member being telescopically received within a portion of said second prosthetic rib member; and stabilizing means for securing said prosthetic rib to said natural ribs of a recipient of said prosthetic rib in an orientation substantially perpendicular to the orientation of said natural ribs to which said prosthetic rib is attached; and locking means operably associated with said first and second rib members for reversibly locking said shaft member to one of a plurality of substantially fixed lengths which are selectible both before and after implantation of said prosthetic rib.

* * * * *